US00PP14698P29

(12) United States Plant Patent
Noodelijk

(10) Patent No.: US PP14,698 P2
(45) Date of Patent: Apr. 13, 2004

(54) CHRYSANTHEMUM PLANT NAMED 'AMOR SPIDER WHITE'

(50) Latin Name: *Chrysanthemum morifolium*
Varietal Denomination: Amor Spider White

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 94 days.

(21) Appl. No.: 10/317,049

(22) Filed: Dec. 12, 2002

(51) Int. Cl.[7] ..... A01H 5/00
(52) U.S. Cl. ..... Plt./287
(58) Field of Search ..... Plt./287

*Primary Examiner*—Anne Marie Grunberg
(74) *Attorney, Agent, or Firm*—Parkhurst & Wendel, L.L.P.

(57) ABSTRACT

A chrysanthemum plant named 'Amor Spider White' characterized by its medium sized blooms with white and yellow ray florets and prolific branching; natural season flower date September 4–9; blooming for a period of 7 weeks.

3 Drawing Sheets

Related cultivars: 'Amor Spider White' is related to 'Amor White' (U.S. Plant patent application Ser. No. 09/734,606). 'Amor Spider White' is a flower form mutant of 'Amor White'.

BACKGROUND OF THE INVENTION

'Amor Spider White' is a product of a breeding and selection program that had the objective of finding mutants of 'Amor White'. The new plant of the present invention comprises a new and distinct cultivar of chrysanthemum plant that is a natural occuring sport of a parent chrysanthemum named 'Amor White' (U.S. Plant patent application Ser. No. 09/734,606). A comparison with Parent chrysanthemum 'Amor White' is also made in this application. The new cultivar was discovered as a sport in September 1999 by Rob Noodelijk in a controlled environment (greenhouse) in Rijsenhout Holland. The first act of asexual reproduction of 'Amor Spider White' was accomplished when vegetative cuttings were taken from the initial selection in October 1999 in Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
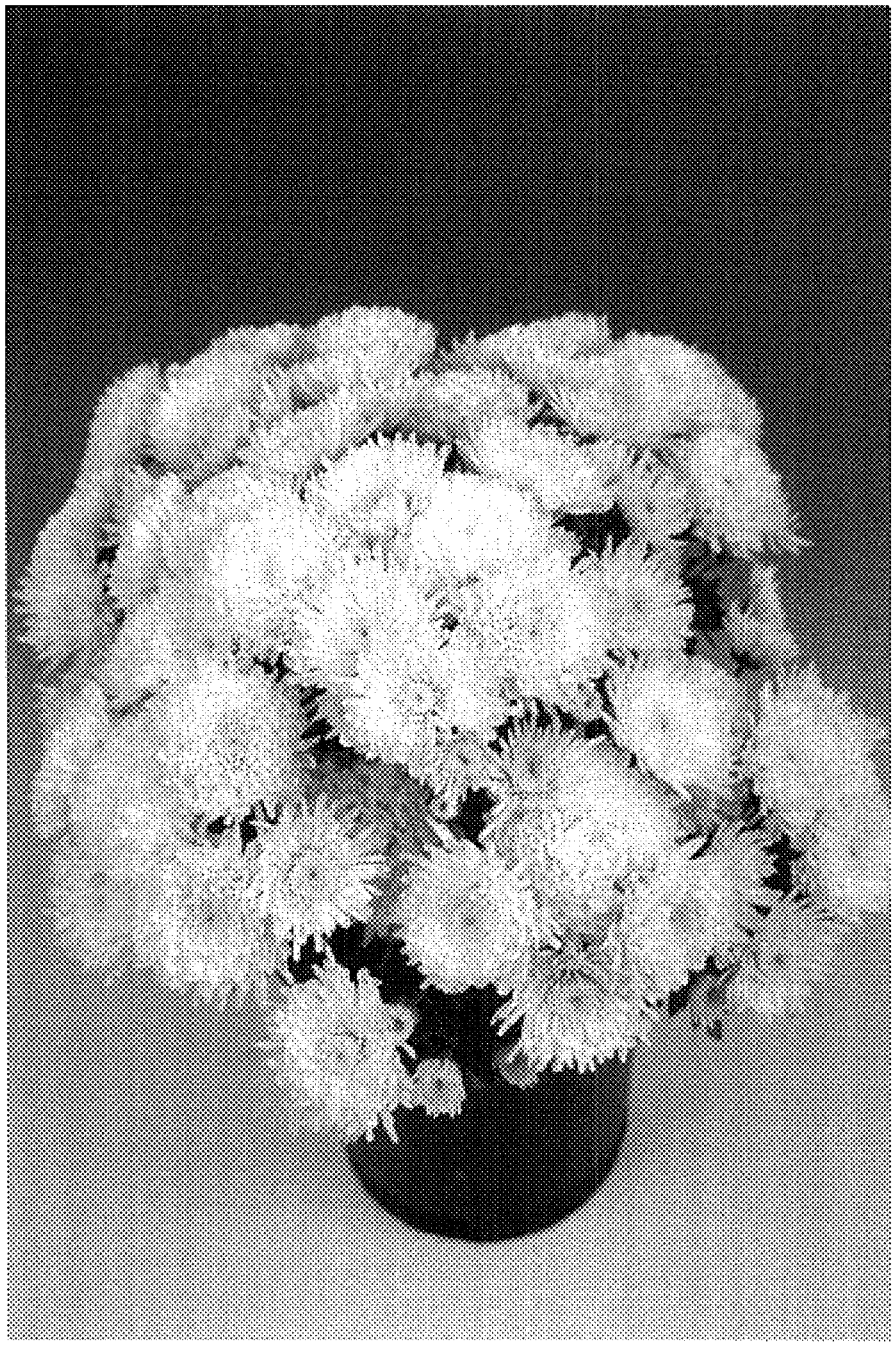
FIG. 1 shows a plant of the cultivar in full bloom.
Figure 2:
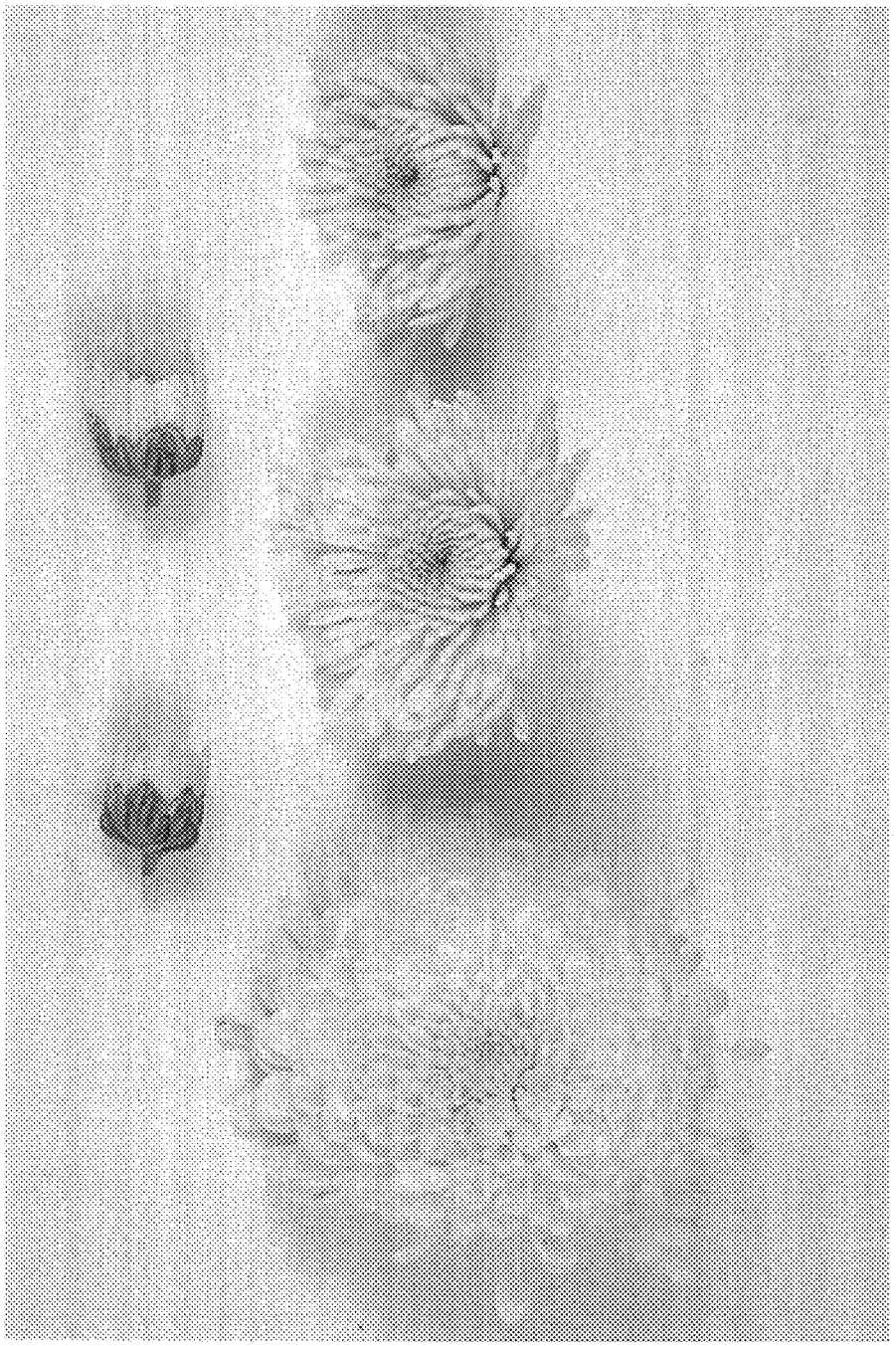
FIG. 2 shows the various stages of bloom of the new cultivar.
Figure 3:
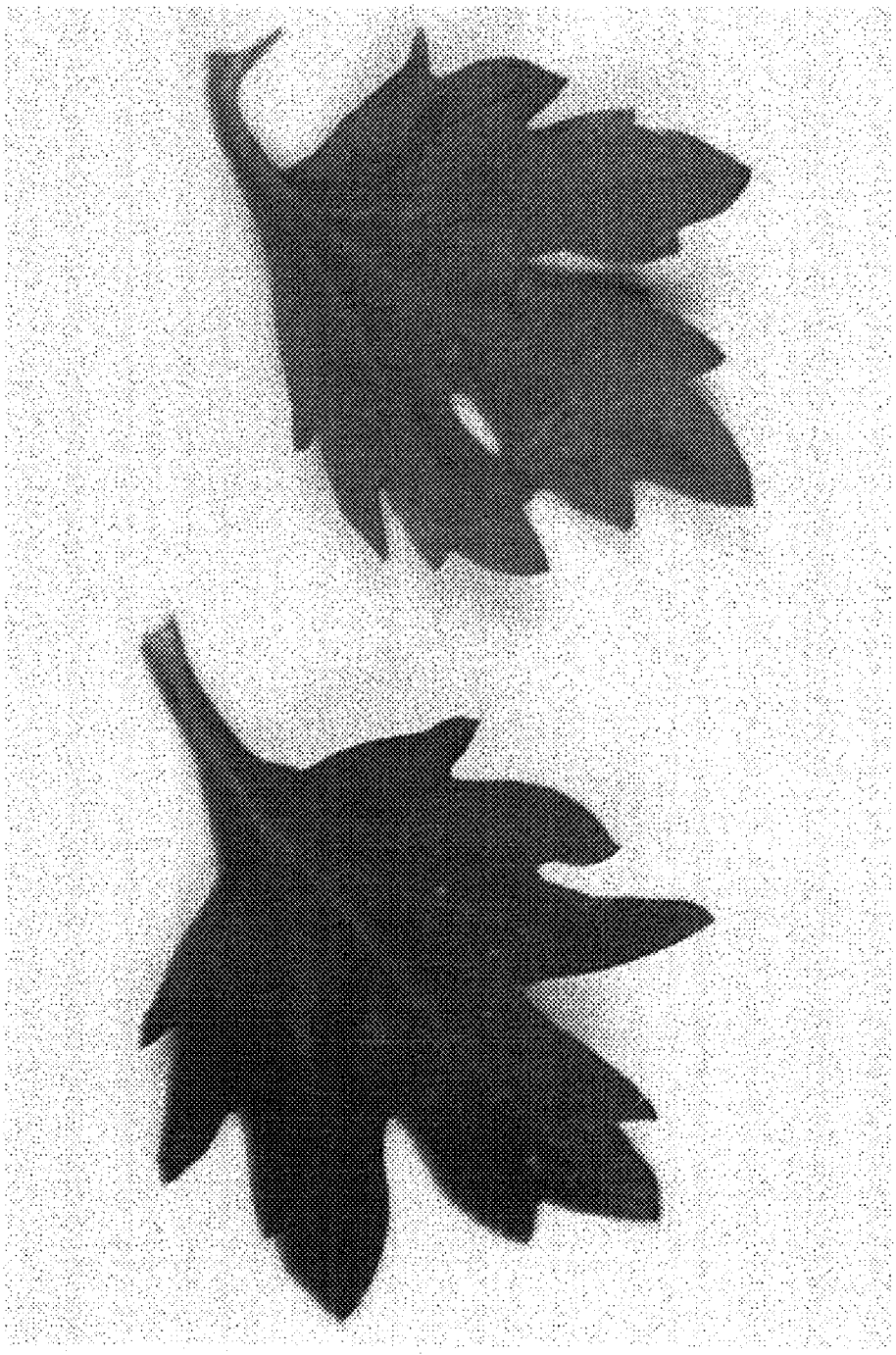
FIG. 3 shows the petiole and foliage of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 2000 and 2001. The natural blooming date of this crop was September 4–9 (week 37). The average height of the plants was 34–38 cms. No growth retardants were used. No tests were done on disease or insects resistance or susceptibility. No tests were done on cold or drought resistance. This new variety produces medium sized blooms with white ray florets and a yellow center blooming for a period of 7 weeks.

When 'Amor White' and 'Amor Spider White' and are being compared the following differences and similarities are noticed: The differences of 'Amor White' and 'Amor Spider White' are (1) Flower form (2) Vigour and (3) Natural flowering date. All other characteristics of 'Amor White' and 'Amor Spider White' are similar (1) Flower color: 'Amor Spider White' is a flower form mutant of 'Amor White'. The ray-florets of 'Amor Spider White' are tubular with a spatulate tip, 'Amor White' has shorter corolla tubes and pointed ray-floret tips.

(2) Vigour: The plants of 'Amor Spider White' tend to be a little more vigorous.

(3) The natural flowering date of 'Amor Spider White' is one week earlier.

The following is a description of the plant and characteristics that distinguish 'Amor Spider White' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1: Botanical Description of Cultivar 'Amor Spider White'

Bud:

*Size.*—Medium; cross-section 1.2 cm, height 1.0 cm.
*Outside color.*—White 155D.
*Involucral bracts.*—2 rows, length 7 mm, width 3 mm.
*Involucral bracts among disc-florets.*—Not present.
*Involucral bracts color.*—Green 138B.

Bloom:

*Type.*—Decorative.
*Height.*—High, 3.0–3.5 cm.
*Size.*—Medium.
*Fully expanded.*—5.5–6.0 cm.

*Number of blooms per branch.*—Approx. 5 blooms per branch.
*Performance on the plant.*—7 weeks.
*Seeds (if crossed).*—Produced in small quantities, ovate Grey-brown 199A, 1½ mm in length.
*Fragrance.*—Typical chrysanthemum, slight.

Color:
*Center of the flower.*—Immature Yellow 8C. Mature Yellow 8C.
*Color of upper surface of the ray-florets.*—White 155D with a pale yellow (8C) part in the center.
*Color of the lower surface of the ray-florets.*—White 155D.
*Tonality from distance.*—A mounded decorative garden mum with white blooms.
*Color of the upper surface of the flowers after aging of the plant.*—White 155D with a pale yellow (8C) part in the center.

Ray florets:
*Texture.*—Upper and under side smooth.
*Number.*—160–180.
*Cross-section.*—Concave.
*Longitudinal axis of majority.*—Incurved (tubular).
*Length of corolla tube.*—Long, 2.0 cm.
*Ray-floret margin.*—Entire.
*Ray-floret length.*—2.5–2.7 cm.
*Ray-floret width.*—0.4 cm.
*Ratio length/width.*—High.
*Shape of tip.*—Spatulate.
*Disc florets.*—Not present.

Reproductive organs:
*Stamen.*—Not present.
*Pollen.*—Not present.
*Styles.*—Thin.
*Style color.*—Yellow-green 144 A.
*Style length.*—4 mm.
*Stigma color.*—Yellow-green 144 A.
*Stigma width.*—1 mm.
*Ovaries.*—Enclosed in calyx.

Plant:
*Shape.*—Grown as a spray-type pot-mum, outdoor mounded and round.
*Growth habit.*—Spreading.
*Growth rate.*—Rapid.
*Height.*—34–38 cm.
*Width.*—32–35 cm.
*Stem color.*—Green 138 B.
*Stem strength.*—Strong.
*Stem brittleness.*—Present.
*Stem anthocyanin coloration.*—Absent.
*Length of lateral branch.*—From top to bottom 14–15 cm.
*Lateral branch color.*—Green 138 B.
*Lateral branch, attachment.*—Weak.
*Branching (average number of lateral branches).*—Mounding and prolific with 8–9 breaks after pinching.
*Peduncle length.*—4.5–5.0 cm.
*Peduncle color.*—Green 138 B.
*Natural season blooming date.*—September 4–9.

Foliage:
*Color of mature leaves.*—Upper side green 138 A. Under side green 138 B.
*Color of immature leaves.*—Upper side green 138 A. Under side green 138 B.
*Size.*—Small; length 6 cm, width 5 cm.
*Quantity (number per lateral branch).*—12–14.
*Shape.*—Oval.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Diverging.
*Shape of base.*—Asymmetric.
*Apex.*—Mucronate.

TABLE 2

Differences with the comparison varieties (when grown under the same conditions)

| | 'AMOR SPIDER WHITE' | 'AMOR WHITE' |
|---|---|---|
| Length of corolla tube | 2.0 cm | 0.9–1.11 cm |
| Shape of tip of ray-florets | Spatulate | Pointed |
| Peduncle length | 4.5–5.0 cm | 4.0–4.5 cm |
| Plant height | 34–38 cm | 32–38 cm |

I claim:

1. A new and distinct variety of chrysanthemum plant as described and illustrated.

* * * * *